United States Patent [19]

Wade et al.

[11] 4,178,451
[45] Dec. 11, 1979

[54] 3-(SUBSTITUTED HYDRAZINO)BENZISOTHIAZOLE-1,1-DIOXIDES

[75] Inventors: Peter C. Wade, Pennington, N.J.; B. Richard Vogt, Yardley, Pa.

[73] Assignee: E. R. Squibb & Sons, Inc., Princeton, N.J.

[21] Appl. No.: 924,257

[22] Filed: Jul. 13, 1978

[51] Int. Cl.$^2$ ............... A61K 31/425; C07D 275/06; C07D 417/12

[52] U.S. Cl. ..................... 546/272; 260/301; 544/405; 544/333; 424/250; 424/251; 424/263; 424/270

[58] Field of Search ............... 260/294.8 C, 301; 544/333, 405

[56] References Cited

U.S. PATENT DOCUMENTS

| 2,751,392 | 6/1956  | Grogan  | 260/301   |
| 3,225,056 | 12/1965 | Traverso | 260/301  |
| 3,271,406 | 9/1966  | Traverso | 260/301  |
| 3,457,272 | 7/1969  | Crook   | 260/301   |
| 3,657,238 | 4/1972  | Skoocz  | 260/247.1 |

Primary Examiner—Alton D. Rollins
Assistant Examiner—Lisa Jones
Attorney, Agent, or Firm—Lawrence S. Levinson; Donald J. Barrack

[57] ABSTRACT

Compounds having the formula

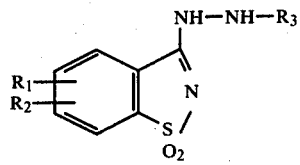

wherein $R_1$ is hydrogen, halogen, alkyl, alkoxy or nitro; $R_2$ is hydrogen, halogen or alkoxy; and $R_3$ is alkoxycarbonyl,

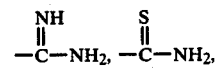

pyridinylcarbonyl, pyrimidinylcarbonyl, or pyrazinylcarbonyl; have antiinflammatory activity.

9 Claims, No Drawings

3-(SUBSTITUTED HYDRAZINO)BENZISOTHIAZOLE-1,1-DIOXIDES

RELATED APPLICATIONS

U.S. Pat. application Ser. No. 799,865, filed May 23, 1977 by Wade and Kissick, now U.S. Pat. No. 4,104,387, issued Aug. 1, 1978, discloses 3-(arylcycloiminoalkyloxy)-benzisothiazole 1,1-dioxides and 3-(arylcycloiminoalkylamino)benzisothiazole 1,1-dioxides having antiinflammatory activity.

U.S. Pat. application Ser. No. 799,879 filed May 23, 1977 by Wade and Kissick, now U.S. Pat. No. 4,104,388, issued Aug. 1, 1978, discloses 3-(cycloimino)-benzisothiazole 1,1-dioxides, 3-(hydroxycycloimino) benzisothiazole 1,1-dioxides and 3-(arylcycloimino)benzisothiazole 1,1-dioxides having antiinflammatory activity.

U.S. Pat. application Ser. No. 875,022, filed Feb. 3, 1978 by Wade and Vogt, now U.S. Pat. No. 4,148,798 discloses [(1,1-dioxo-1,2-benzisothiazol-3-yl)amino]alkanoic acids and esters thereof, and [(1,1-dioxo-1,2-benzisothiazol-3-yl)amino]cycloalkanoic acids and esters thereof, having antiinflammatory activity.

U.S. Pat. application Ser. No. 875,021, filed Feb. 3, 1978 by Wade, Vogt and Kissick, now U.S. Pat. No. 4,104,693, issued Feb. 20, 1979, discloses 2,3-dihydro-1,2,4-triazolo[4,3-b][1,2]benzisothiazol-3-amine, 5,5-dioxide having antiinflammatory activity.

U.S. Pat. application Ser. No. 875,020, filed Feb. 3, 1978 by Wade and Kissick, discloses 3-(substituted hydrazino)benzisothiazole 1,1-dioxides having the formulas

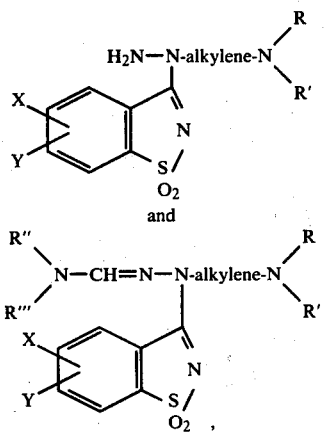

wherein X is hydrogen, halogen, alkyl, alkoxy or nitro, Y is hydrogen, halogen, or alkoxy and each of the —NRR groups is dialkylamino or a 5— or 6—membered heterocycle. The compounds have antiinflammatory activity.

U.S. Pat. application Ser. No. 875,018, filed Feb. 3, 1978 by Wade, Vogt, and Kissick, now U.S. Pat. No. 4,108,860, issued Aug. 22, 1978, discloses 1,2,4-triazolo[4,3-b][1,2]benzisothiazole, 5,5-dioxides and 3-aryl and 3-alkyl derivatives having antiinflammatory activity.

BACKGROUND OF THE INVENTION

U.S. Pat. No. 2,751,392 issued June 19, 1956, discloses, inter alia, compounds having the formula

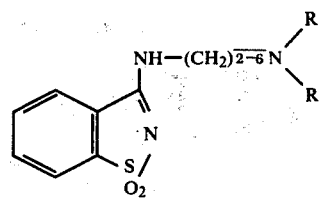

wherein R is alkyl or the —NRR grouping can be a heterocyclic ring. The compounds are said to have analgesic and antihistaminic activity.

U.S. Pat. No. 3,225,056 issued Dec. 21, 1965, discloses inter alia, 3-(substituted hydrazino)benzisothiazoles having the formula

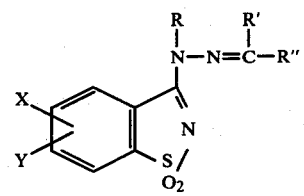

wherein X and Y are hydrogen, halogen, alkyl, alkoxy or trifluoromethyl; R and R' when taken alone are hydrogen; R" when taken alone is alkyl or alkenyl; R' and R" taken together with the carbon atom to which they are attached form a cyclopentyl or cyclohexyl ring; and R and R' when taken together with the

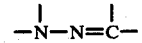

grouping to which they are attached form a heterocyclic ring. The above compounds are said to have hypotensive and diuretic activity.

U.S. Pat. No. 3,271,406 issued Sept. 4, 1966, discloses 3-(substituted hydrazino)benzisothiazoles having the formula

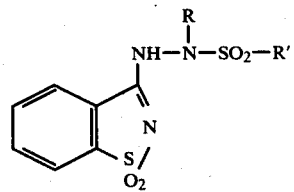

wherein R is hydrogen, alkyl or alkenyl and R' is alkyl, phenyl, α-naphthyl or β-naphthyl. The compounds are said to have hypotensive activity.

U.S. Pat. No. 3,457,272 issued July 22, 1969, discloses, inter alia, N-substituted-1,2-benzisothiazole-3-one, 1,1-dioxides. The compounds are said to exhibit various central nervous system activities.

BRIEF DESCRIPTION OF THE INVENTION

Compounds having the formula

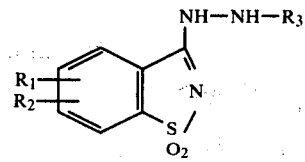

have antiinflammatory activity. In formula I, and throughout the specification, the symbols are as defined below.

$R_1$ is hydrogen, halogen, alkyl, alkoxy, or nitro and $R_2$ is hydrogen, halogen or alkoxy, with the proviso that if $R_2$ is other than hydrogen, $R_1$ and $R_2$ are the same; and $R_3$ is

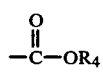   (i)

wherein $R_4$ is alkyl of 1 to 6 carbon atoms or cycloalkyl of 3 to 7 carbon atoms,

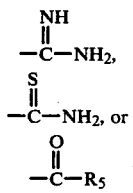

wherein $R_5$ is 2—,3— or 4—pyridinyl, 2—,4—, or 5-pyrimidinyl or 2-pyrazinyl.

The terms "alkyl" and "alkoxy", as used throughout the specification (unless otherwise defined), refer to groups having 1 to 4 carbon atoms; groups having 1 or 2 carbon atoms are preferred.

The term "halogen", as used throughout the specification, refers to fluorine, chlorine, bromine and iodine; chlorine and bromine are preferred.

DETAILED DESCRIPTION OF THE INVENTION

The compounds of formula I can be prepared by reacting a 3-halo-1,2-benzisothiazole, 1,1-dioxide having the formula

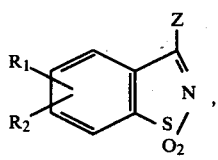   II wherein Z is halogen (chlorine being the most preferred) with a compound having the formula

   III

The reaction can be run in an organic solvent, e.g., dioxane, benzene, dimethylformamide, dimethoxyethane or the like.

The starting materials of formula III are known in the art. Some of the starting materials are commercially available and all of them are readily obtainable via conventional synthetic routes.

The 3-halo-1,2-benzisothiazole, 1,1-dioxides of formula II are also known in the art; see, for example, U.S. Pat. No. 3,225,056, issued Dec. 12, 1965. They can be prepared from the corresponding saccharin compound having the formula

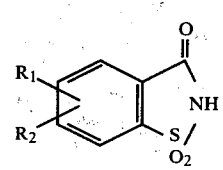   IV by reaction with thionyl chloride in an inert organic solvent, preferably with a catalytic amount of dimethylformamide.

The compounds of formula I wherein $R_3$ is

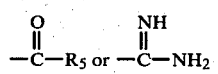

can be converted into pharmaceutically acceptable salts using art recognized procedures. Acid-addition salts are specifically contemplated, e.g., the hydrohalides (particularly hydrochloride and hydrobromide), sulfate, nitrate, phosphate, tartrate, maleate, fumarate, citrate, succinate, methanesulfonate, benzenesulfonate, toluenesulfonate and the like.

The compounds of formula I, and the pharmaceutically acceptable salts thereof, can be used to treat inflammation in mammals. Joint tenderness and stiffness (in conditions such as rheumatoid arthritis) can be reduced by these compounds.

The compounds of this invention can be formulated for use as antiinflammatory agents according to accepted pharmaceutical practice in oral dosage forms such as tablets, capsules, elixirs or powders, or in an injectable form in a sterile aqueous vehicle. The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The following examples are specific embodiments of this invention.

EXAMPLE 1

2-(1,2-Benzisothiazol-3-yl)hydrazinecarboxylic acid, methyl ester, S,S-dioxide

Methylhydrazinocarboxylate (2.08g.) is dissolved in 15 ml. of dioxane and added to 6.0 g. of 3-chloro-1,2-benzisothiazole, 1,1-dioxide dissolved in 50 ml of dioxane. The mixture is refluxed for 30 minutes and stirred for about 16 hours at room termperature. The product which precipitates out is filtered off, recrystallized from 200 ml of water and dried at 110° C., in vacuo, for 5 hours, yielding 3.8 g. of material, melting point 234° C.-235° C.

EXAMPLE 2

4-Pyridinecarboxylic acid, 2-(1,1-dioxo-1,2-benzisothiazol-3-yl)hydrazide

3-Chloro-1,2-benzisothiazole, 1,1-dioxide (6.0g.) and 4.09 g. of isonicotinic acid hydrazide are refluxed in 200 ml of dioxane for 30 minutes. After cooling to room temperature, the precipitate is filtered off and suspended in 600 ml of water. The material dissolves when the mixture is made basic with 10% sodium hydroxide. The precipitate that is formed by acidifying the solution with 10% hydrochloric acid is filtered off, washed with water and dried for 5 hours at 100° C., in vacuo, yielding 2.4 g of the title compound, melting point 288°–289° C.

EXAMPLE 3

2-(1,1-Dioxo-1,2-benzisothiazol-3-yl)hydrazinecarboximidamide

3-Chloro-1,2-benzisothiazole, 1,1-dioxide (10.0 g.) and 6.76 g. of aminoguanidine bicarbonate are refluxed in 300 ml of dioxane for 1 hour. After cooling to room temperature, the precipitate is filtered off, washed with dioxane, suspended in 700 ml of water and dissolved by adding sufficient 50% sodium hydroxide. The product is precipitated by adding concentrated hydrochloric acid (to pH 6), filtered out, washed with water and recrystallized from 75 ml of dimethylformamide-50 ml of ethanol, yielding 3.67 g. of the title compound, melting point 252°–253° C.

EXAMPLES 4-10

Following the procedure of Example 1, but substituting the compound listed in column I for 3-chloro-1,2-benzisothiazole, 1,1-dioxide and the compound listed in column II for methylhydrazinocarboxylate, yields the compound listed in column III.

| | Column I | Column II | Column III |
|---|---|---|---|
| 4 | 3,5,6,-trichloro-1,2 benzisothiazole, 1,1-dioxide | cyclopropylhydrazinocarboxylate | 2-(5,6-dichloro-1,2-benzisothiazol-3-yl)hydrazinecarboxylic acid, cyclopropyl ester, S,S-dioxide |
| 5 | 3-chloro-5-methyl-1,2-benzisothiazole, 1,1-dioxide | hexylhydrazinocarboxylate | 2-(5-methyl-1,2-benzisothiazol-3-yl)hydrazinecarboxylic acid, hexyl ester, S,S-dioxide |
| 6 | 3-chloro-5,6-dimethoxy-1,2-benzisothiazole, 1,1-dioxide | (1-methylethyl)-hydrazinocarboxylate | 2-(5,6-dimethoxy-1,2-benzisothiazol-3-yl)-hydrazinecarboxylic acid, 1-methylethyl ester, S,S-dioxide |
| 7 | 3-chloro-5-nitro-1,2-benzisothiazole, 1,1-dioxide | nicotinic acid hydrazide | 3-pyridinecarboxylic acid, 2-(1,1-dioxo-5-nitro-1,2-benzisothiazol-3-yl) hydrazide |
| 8 | 3-chloro-5-methoxy-1,2-benzisothiazole, 1,1-dioxide | 2-pyrazinecarboxylic acid hydrazide | 2-pyrazinecarboxylic acid, 2-(1,1-dioxo-5-methoxy-1,2-benzisothiazol-3-yl)hydrazide |
| 9 | 3-chloro-1,2-benzisothiazole, 1,1-dioxide | 4-pyrimidinecarboxylic acid hydrazide | 4-pyrimidinecarboxylic acid, 2-(1,1-dioxo-1,2-benzisothiazol-3-yl) hydrazide |
| 10 | 3-chloro-1,2-benzisothiazole, 1,1-dioxide | thiosemicarbazide hydrochloride | 2-(1,1-dioxo-1,2-benzisothiazol-3-yl)hydrazinethiocarboxamide |

What is claimed is:

1. A compound having the formula

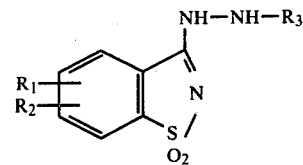

wherein:

$R_1$ is hydrogen, halogen, alkyl of 1 to 4 carbon atoms, alkoxy of 1 to 4 carbon atoms, or nitro and $R_2$ is hydrogen, halogen, or alkoxy of 1 to 4 carbon atoms, provided that if $R_2$ is other than hydrogen, $R_1$ and $R_2$ are the same; and $R_3$ is

 (i)

wherein $R_4$ is alkyl of 1 to 6 carbon atoms or cycloalkyl of 3 to 7 carbon atoms,

 (ii)

 (iii)

 (iv)

wherein $R_5$ is 2-pyridinyl, 3-pyridinyl, 4-pyridinyl, 2-pyrimidinyl, 4-pyrimidinyl, 5-pyrimidinyl, or 2-pyrazinyl; or a pharmaceutically acceptable salt of those compounds wherein $R_3$ is

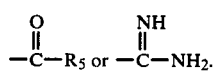

2. A compound in accordance with claim 1 wherein $R_3$ is

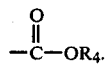

3. A compound in accordance with claim 1 wherein $R_3$ is

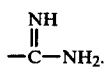

4. A compound in accordance with claim 1 wherein $R_3$ is

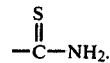

5. A compound in accordance with claim 1 wherein $R_3$ is

6. A compound in accordance with claim 5 wherein $R_5$ is 4-pyridinyl.

7. The compound in accordance with claim 1 having the name 2-(1,2-benzisothiazol-3-yl)hydrazinecarboxylic acid, methyl ester, S,S-dioxide.

8. The compound in accordance with claim 1 having the name 4-pyridinecarboxylic acid, 2-(1,1-dioxo-1,2-benzisothiazol-3-yl)hydrazide.

9. The compound in accordance with claim 1 having the name 2-(1,1-dioxo-1,2-benzisothiazol-3-yl)hydrazinecarboximidamide.

* * * * *